United States Patent [19]

Haemmerle et al.

[11] 3,980,448
[45] Sept. 14, 1976

[54] ORGANIC COMPOUNDS FOR USE AS FUEL ADDITIVES

[75] Inventors: Bernard Haemmerle; Bernard Sillion; Gabriel De Gaudemaris, all of Grenoble, France

[73] Assignee: Institut Francais du Petrole, des Carburants et Lubrifiants et Entreprise de Recherches et d'Activities Petrolieres Elf, Rueil-Malmaison, France

[22] Filed: May 2, 1973

[21] Appl. No.: 356,508

Related U.S. Application Data

[62] Division of Ser. No. 127,047, March 22, 1971, abandoned.

[52] U.S. Cl. .................. 44/63; 44/DIG. 1; 44/DIG. 4; 252/394
[51] Int. Cl.² ............................................. C10L 1/26
[58] Field of Search .............. 44/63, DIG. 1, DIG. 4; 260/326.5 F, 326.5 FM; 252/394; 208/17

[56] References Cited
UNITED STATES PATENTS

| | | | |
|---|---|---|---|
| 3,280,033 | 10/1966 | Drummond | 252/51.5 |
| 3,341,542 | 9/1967 | Le Suer | 260/268 C |
| 3,346,492 | 10/1967 | Hess | 44/63 |
| 3,382,056 | 5/1968 | Mehmedbasich | 44/63 |
| 3,401,118 | 9/1968 | Benoit | 252/51.5 |
| 3,655,351 | 4/1972 | Jamieson | 44/63 |
| 3,657,397 | 4/1972 | Brannen | 44/DIG. 4 |
| 3,676,089 | 7/1972 | Morris et al. | 44/63 |
| 3,702,757 | 11/1972 | Mehmedbasich | 44/DIG. 1 |

FOREIGN PATENTS OR APPLICATIONS 1,499,785  10/1967  France .............................. 260/326.5

*Primary Examiner*—Daniel E. Wyman
*Assistant Examiner*—Y. H. Smith
*Attorney, Agent, or Firm*—Millen, Raptes & White

[57] ABSTRACT

This invention relates to gasoline compositions containing additives which are reaction products of a maleic anhydride of the formula

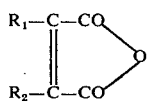

with a linear polyamine of the formula

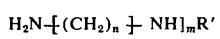

in which $R_1$ and $R_2$ are selected from the group consisting of a hydrogen atom and a monovalent hydrocarbon radical of 1 – 30 carbon atoms, $R'$ is a monovalent aliphatic hydrocarbon radical having 6 – 30 carbon atoms, $n$ is an integer from 3 to 10 and $m$ is an integer from 1 to 10.

21 Claims, No Drawings

ORGANIC COMPOUNDS FOR USE AS FUEL ADDITIVES

This is a division of application Ser. No. 127,047, filed Mar. 22, 1971, now abandoned.

This invention is related to fuel compositions containing novel additives.

This invention relates specifically to the use of reaction products of maleic anhydrides and polyamines and alkyl phosphoric acid neutralization products thereof as detergent, antifrost and anti-corrosion additives in fuel compositions, specially those used in spark-ignited engines.

Another object of this invention is the use of reaction products of the maleic anhydride-amine reaction product type associated with mineral lubricating oils, as additives in fuel compositions, these compounds having cleaning properties in addition to the said detergent, antifrost and anti-corrosion properties.

Many carburation problems are raised by the use of fuels of the gasoline type, particularly in motor-car engines. Thus important deposits are frequently formed on the carburetor elements of motor-car engines, specially in town traffic or at high temperature. These deposits are responsible of misfiring and engine stalling. They are even more troublesome when using devices for the sweeping of crankcase gases known as "Positive Crankcase Ventilation" (PCV), in order to reduce the atmospheric pollution.

When particular hygrometric conditions and air temperatures are met, ice crystals are formed on the walls of the carburetor to which they adhere. They can accumulate in such an amount as to obstruct the passage at the throttle valve level.

Finally, the water dissolved in the gasoline may corrode the metal parts of the engine.

To cope with these difficulties, additives have been added to gasoline in relatively small amounts, for example about 50 parts per million of parts by weight. The main functions of these additives are: to avoid deposits to be formed in the carburetor (detergent effect), to prevent the adherence of ice crystals on the metal walls (antifrost effect) and to form a protective film on the engine parts (anti-corrosion effect).

In order to obtain these effects with one molecule only, several additives have been proposed, said additives consisting of organic compounds whose molecule, as a rule, comprises at least one linear portion, soluble in gasoline, and at least one polar portion.

The new organic nitrogen-containing reaction products of this invention, when dissolved in a fuel, form improved detergents, antifrost agents and corrosion inhibitors, and have other advantages which will appear hereinafter.

These compounds are reaction products of a maleic anhydride of the formula

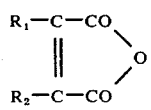

with a linear polyamine of the formula

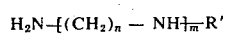

in which $R_1$ and $R_2$ are selected from the group consisting of the hydrogen atom and the straight or branched monovalent hydrocarbon radicals, the total number of carbon atoms of $R_1$ and $R_2$ being from 0 to 30, $n$ is an integer from 3 to 10, $m$ is an integer from 1 to 10 and $R'$ is a straight or branched, saturated or unsaturated, aliphatic hydrocarbon monovalent radical, the number of carbon atom being in the range from 6 to 30.

For example maleic anhydride may be reacted with N-oleyl propane diamine or with N-stearyl propane diamine or a mixture of both. Maleic anhydride derivatives, for example dimethyl-, diethyl- or di-n-butyl-maleic anhydride, may be reacted with these diamines or their mixtures.

The reaction may be carried out in an inert solvent, for example an aromatic hydrocarbon or a mixture of aromatic hydrocarbons at a temperature preferably lower than 55°C. Benzene, toluene, xylenes and their mixtures may be used.

The water evolving during the reaction may be removed, for example by azeotropic distillation when the selected solvent forms an azeotropic mixture with water.

Furthermore, it has been observed that the reaction products when associated with compounds of alkylphosphoric acid type, increase the number of polar groups and provide for a greater solubility of the additive in the mixtures of aromatic solvents and an improvement of some of the above effects, particularly the antifrost effect.

The present invention also relates to the compounds resulting from the neutralization of a maleimide-amine reaction products with at least one alkylphosphoric acid, as follows:

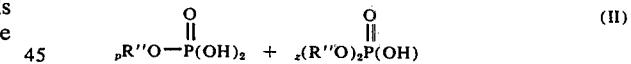

wherein $R''$ is a straight or branched aliphatic hydrocarbon radical having from 8 to 18 carbon atoms, and $p$ and $z$ are integers such that the total number of the OH groups of the acids is not in excess of the number of amine groups of the maleimide-amine reaction product.

Among the alkyl phosphoric acids which may be used, the mixtures of monoalkyl- and dialkyl-phosphoric acids obtained by reacting phosphoric anhydride with an alcohol or a mixture of straight or branched aliphatic alcohols are preferred.

This reaction may be illustrated by the following formulae:

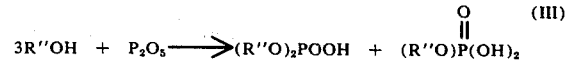

in which R'' is a straight or branched alkyl radical having from 8 to 18 carbon atoms. Particular alcohols may be selected so as to obtain a fuel composition which is not liable to extraction with water. Such branched alcohols as, for example, ethylhexyl alcohol may be used in that case.

The neutralization reaction, when applied to a maleimide-amine reaction product, may be carried out by adding the alkylphosphoric acid to a solution of said maleimide-amine in an aromatic solvent, while maintaining the reaction mixture for several hours at a temperature of about 10° to 65°C.

The maleimides-amine reaction products, either as such or at least partially neutralized with alkylphosphoric acids, may be added to the fuel compositions at concentrations of 10 to 250 and preferably 10 to 100 parts per million of parts by weight, without loss of limpidity, even if added at a low temperature. These compounds may be used in association with usual additives without trouble.

The maleimides-amine reaction products of this invention, when used in a fuel composition in association with a small amount of at least one mineral oil, also have cleaning properties. There are used, for example, from 50 to 2000 ppm by weight of a mineral lubricating oil such as, for example, a naphthenic oil and from 10 to 250 ppm by weight of at least one compound according to this invention.

The following examples are given by way of mere illustraton:

EXAMPLE 1

32.4 g of N-oleyl propane diamine (0.1 mole) and 9.8 g of maleic anhydride (0.1 mole) are dissolved in 100 ccm of a mixture of toluene and xylene in equal volumes. The solution is heated at reflux until all the reaction water has been carried away by azeotropic distillation. 1.8 g of water is recovered and a solution of a reaction product is obtained. The volume of the solution is adjusted to a known volume by means of the above mixture of solvents, so as to obtain a titrated solution.

EXAMPLE 2

17.7 g (about 0.1 hydroxy equivalent) of an equimolar mixture of mono- and di-octyl phosphoric acids are added to the above solution, the temperature being kept below 65°C. The reaction mixture is thereafter maintained at 80°–85°C for 1 hour under strong stirring. The resulting oily product is diluted to a known volume by means of the 50/50 toluene-xylene mixture, thus resulting in a titrated solution.

EXAMPLE 3

84.6 Kg of xylene, 0.1 Kg of hydroquinone, 83.2 Kg of an equimolar mixture of N-oleyl propane diamine and N-stearyl propane diamine (Trade Mark DINORAM - S) and 21.5 Kg of maleic anhydride are introduced into a glass reaction vessel of a 200 liters volume. The introduction time is 8 hours at a temperature of 45°–50°C. The pink reaction mixture is subjected to further heating and, when a temperature of 75°–80°C is attained, the color turns to reddish violet. The temperature is further increased up to the xylene reflux temperature. After 5 hours of azeotropic distillation of water and xylene, 5.2 kg of water are collected.

After cooling, a solution of a mixture of reaction products is obtained. Xylene is added to complete the volume and the resulting solution is divided into two equal fractions.

EXAMPLE 4

One of the fractions of example 3 is admixed with an equimolar mixture of the mono- and di-octyl phosphoric acids, in an amount of 19 kg i.e. an amount corresponding substantially to all of the amine groups convertible to salts in said mixture of the maleic anhydride-amine reaction products. During this operation, the temperature is maintained below 65°C. The stirred reaction mixture is further heated up to 80°–85°C and maintained at this temperature for 1 hour. The resulting oily mixture is brought to a known volume by addition of xylene.

EXAMPLE 5

Determination of carburetor performance.

There is used an engine of the Renault R 16-69 701 type with a Solex carburetor of the 35 D.I.T.A. 2 type. This engine is lubricated with a conventional 20 W/40 multigrade oil and fed with a premium gasoline whose composition by weight is the following:

| - Aromatic hydrocarbons | 38 % |
| - Olefins | 1 % |
| - saturated hydrocarbons | 61 % |

This gasoline further contains 0.48 g of lead per liter.

The engine is operated for 48 hours with a 10 to 12 % recycling rate of the exhaust gases. About 200 liters of premium gasoline are consumed during each experiment.

In each experiment, there is used a new carburetor (i.e. with a merit of 10). The carburetor is fouled at the end of the experiment and its merit is determined.

The results of the experiments carried out with the use of said premium gasoline are summarized in table I:
1. without detergent
2. with 45 ppm, by weight of the reaction product of example 3
3. with 45 ppm by weight of the reaction product of example 4
4. with 150 ppm by weight of the reaction product of example 3
5. with 150 ppm by weight of the reaction product of example 3 and 600 ppm by weight of a naphthenic oil having a viscosity of 293.5 cSt at 100°F and 16.25 cSt at 210°F.

TABLE I

| Type of gasoline | (1) | (2) | (3) | (4) | (5) |
|---|---|---|---|---|---|
| Carburetor merit | 3.8 | 6.6 | 6.5 | 8.9 | 8.1 |
| Merit increase* | | 2.8 | 2.7 | 5.1 | 4.3 |

*The merit increase is the difference between the merits observed respectively with and without additives.

EXAMPLE 6

Carburetor cleaning test

The engine and the carburetor type of example 1 are used again and the carburetor is subjected to fouling by running the engine for 48 hours with the same premium gasoline without additive and by recycling from 15 to 17 % of the exhaust gases.

At the end of this fouling period, the merit of the carburetor has decreased from the initial value of 10 to 2.

The engine is operated for 23 more hours under normal running conditions with the use of premium gasoline containing 250 ppm by weight of the compound of example 3 and 600 ppm by weight of the same naphthenic oil as in the above example.

At the end of this operating cycle, the carburetor merit is 6.4, corresponding to a merit increase by 4.4 over the initial merit value of 2 at the beginning of the cycle.

EXAMPLE 7

Carbon Monoxide Content of Off-Gases

The carburetor is subjected to fouling, as shown in example 6. Table II indicates the carbon monoxide content at the beginning of the test and after a 30 hours fouling period.

TABLE II

| Time | Engine speed | % CO by volume in the off-gases |
|---|---|---|
| 0 hour | 650 r.p.m. | 3.75 |
|  | 1 300 r.p.m. | 3.55 |
| 30 hours | 650 r.p.m. | <10 |
|  | 1 300 r.p.m. | 5.3 |

The engine is then operated at normal running conditions with the use of premium gasoline containing 250 ppm by weight of the reaction product of example 3 and 650 ppm by weight of the naphthenic oil of example 5.

The carbon monoxide content is given in table III.

TABLE III

| Time | Engine speed | % CO by volume in the off-gases |
|---|---|---|
| 24 hours | 650 r.p.m. | 3 |
|  | 1 300 r.p.m. | 4.6 |

EXAMPLE 8

Determination of the anti-frost properties

The method was I.F.P.'s method as described in "Carburants et Combustibles pour moteurs a combustion interne" by J. WEISSMANN, Technip editor (1970), the premium gasoline being that of example 5. The additive was as described in example 3 and various concentrations thereof were used. The results are given in table IV.

TABLE IV

| | Icing | |
|---|---|---|
| | Idling | Road |
| Fuel | Time necessary for stalling (seconds) | Time necessary for stopping (minutes) |
| Gasoline alone | 40 – 50 | 20 |
| Gasoline + 150 ppm of additive | >120 | >60 |
| Gasoline + 150 ppm of additive+600ppm of oil* | 80 – 90 | >60 |
| Gasoline + 45 ppm of additive | 80 | 45 |

*The oil was the naphthenic oil described in example 5

EXAMPLE 9

Anti-corrosion test (ASTM method D - 665 - 60)

30 cc of synthetic sea water are added to 300 cc of gasoline containing 45 ppm by weight of the compound of example 3. The resulting mixture is maintained at 100°F for 24 hours in the presence of a polished steel rod.

After the test the rod remained clear.

Similarly one part of carburetor remains clear.

When using gasoline without additive, under the same conditions, the steel rod and the carburetor metal are covered with oxides.

EXAMPLES 10 to 20

In these examples, maleimides-amine reaction products according to the present invention have been manufactured.

These reaction products have been incorporated in gasolines and tested according to the methods of examples 5 to 9.

The reaction products were those obtained by reacting a maleic anhydride with a polyamine of the general formula given hereinbefore, wherein $R_1$, $R_2$, $n$, $m$ and $R'$ are defined as follows:

| Example No | $R_1$ | $R_2$ | n | m | R' |
|---|---|---|---|---|---|
| 10 | $CH_3$ | $CH_3$ | 3 | 1 | oleyl |
| 11 | dodecyl | dodecyl | 3 | 1 | oleyl |
| 12 | H | H | 5 | 1 | stearyl |
| 13 | H | H | 8 | 1 | stearyl |
| 14 | H | H | 10 | 1 | oleyl |
| 15 | $C_2H_5$ | $C_2H_5$ | 3 | 2 | oleyl |
| 16 | $C_3H_7$ | $C_3H_7$ | 3 | 5 | oleyl |
| 17 | $C_6H_{13}$ | $C_6H_{13}$ | 3 | 10 | oleyl |
| 18 | H | H | 3 | 1 | hexyl |
| 19 | H | H | 3 | 1 | dodecyl |
| 20 | H | H | 3 | 1 | eicosyl |

The results were substantially the same as those of examples 5 to 9

In this specification, stearyl means octadecyl-1 ($C_{18}H_{37}$) and oleyl means 9-octadecenyl-1 ($C_{18}H_{35}$).

What we claim as this invention is:

1. A fuel composition comprising a major amount of gasoline and, as an additive, an amount sufficient to result in an improvement of carburetor anti-fouling properties of said composition, of at least one imidic reaction product of a maleic anhydride of the formula

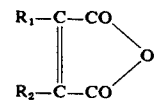

with a substantially equimolar quantity of a linear polyamine of the formula

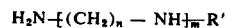

in which $R_1$ and $R_2$ are selected from the group consisting of a hydrogen atom and an alkyl radical of 1–30 carbon atoms, the total number of carbon atoms of $R_1$ and $R_2$ being not more than 30, R' is an alkyl or alkenyl radical having 6–30 carbon atoms, $n$ is an integer from 3 to 10 and $m$ is an integer from 1 to 10, said reaction being conducted in an inert solvent and wherein the water resulting from the reaction is removed therefrom.

2. A fuel composition as defined by claim 1, wherein said reaction product represents from 10 to 250 parts per million of parts by weight of said gasoline.

3. A fuel composition as defined by claim 1, wherein said reaction product is in the form of its neutralization product with an amount of at least one acid compound selected from the group consisting of monoalkyl- and dialyky- phosphoric acids of the general formulae:

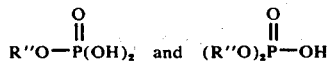

in which R'' is a monovalent radical of a saturated aliphatic hydrocarbon having from 8 to 18 carbon atoms, corresponding to a number of OH groups not higher than the number of amine groups of said compound.

4. A fuel composition as defined by claim 3, wherein said neutralization product represents, by weight, from 10 to 250 parts per million of parts of the gasoline.

5. A fuel composition as defined by claim 1, further comprising an amount of at least one naphthenic mineral oil sufficient to yield cleaning properties to said composition in combination with said reaction product.

6. A fuel composition as defined by claim 5, wherein said mineral oil represents, by weight, from 50 to 2000 parts per million of parts of the gasoline.

7. A fuel composition as defined by claim 1, wherein $R_1$ and $R_2$ are $CH_3$, $n$ is 3, $m$ is 1, and R' is oleyl.

8. A fuel composition as defined by claim 1, wherein $R_1$ and $R_2$ are dodecyl, $n$ is 3, $m$ is 1, and R' is oleyl.

9. A fuel composition as defined by claim 1, wherein $R_1$ and $R_2$ are H, $n$ is 5, $m$ is 1, and R' is stearyl.

10. A fuel composition as defined by claim 1, wherein $R_1$ and $R_2$ are H, $n$ is 8, $m$ is 1, and R' is stearyl.

11. A fuel composition as defined by claim 1, wherein $R_1$ and $R_2$ are H, $n$ is 10, $m$ is 1, and R' is oleyl.

12. A fuel composition as defined by claim 1, wherein $R_1$ and $R_2$ are $C_2H_5$, $n$ is 3, $m$ is 2, and R' is oleyl.

13. A fuel composition as defined by claim 1, wherein $R_1$ and $R_2$ are $C_3H_7$, $n$ is 3, $m$ is 5, and R' is oleyl.

14. A fuel composition as defined by claim 1, wherein $R_1$ and $R_2$ are $C_6H_{13}$, $n$ is 3, $m$ is 10, and R' is oleyl.

15. A fuel composition as defined by claim 1, wherein $R_1$ and $R_2$ are H, $n$ is 3, $m$ is 1, and R' is hexyl.

16. A fuel composition as defined by claim 1, wherein $R_1$ and $R_2$ are H, $n$ is 3, $m$ is 1, and R' is dodecyl.

17. A fuel composition as defined by claim 1, wherein $R_1$ and $R_2$ are H, $n$ is 3, $m$ is 1, and R' is eicosyl.

18. A fuel composition as defined by claim 3, wherein said acid compound is a mixture of mono- and di-octyl phosphoric acids.

19. The fuel composition of claim 1, wherein the inert solvent consists essentially of at least one aromatic hydrocarbon forming with water an azeotropic mixture, and the water resulting from the reaction is removed by azeotropic distillation.

20. A fuel composition according to claim 1, wherein maleic anhydride is reacted with N-oleyl propane diamine.

21. A fuel composition according to claim 1, wherein maleic anhydride is reacted with N-stearyl propane diamine.

* * * * *

UNITED STATES PATENT AND TRADEMARK OFFICE
CERTIFICATE OF CORRECTION

PATENT NO. : 3,980,448
DATED : September 14, 1976
INVENTOR(S) : Bernard Haemmerle et al.

It is certified that error appears in the above-identified patent and that said Letters Patent are hereby corrected as shown below:

[73] Assignee: show read --INSTITUT FRANCAIS DU PETROLE--.

Signed and Sealed this

First Day of February 1977

[SEAL]

Attest:

RUTH C. MASON
*Attesting Officer*

C. MARSHALL DANN
*Commissioner of Patents and Trademarks*